(12) United States Patent
Demarest et al.

(10) Patent No.: US 9,057,670 B2
(45) Date of Patent: Jun. 16, 2015

(54) TRANSMISSION ELECTRON MICROSCOPE SAMPLE FABRICATION

(71) Applicant: International Business Machines Corporation, Armonk, NY (US)

(72) Inventors: James J. Demarest, Rensselaer, NY (US); Juntao Li, Guilderland, NY (US)

(73) Assignee: International Business Machines Corporation, Armonk, NY (US)

( * ) Notice: Subject to any disclaimer, the term of this patent is extended or adjusted under 35 U.S.C. 154(b) by 16 days.

(21) Appl. No.: 13/905,289

(22) Filed: May 30, 2013

(65) Prior Publication Data

US 2014/0353497 A1    Dec. 4, 2014

(51) Int. Cl.
| | |
|---|---|
| G01N 1/28 | (2006.01) |
| H01J 37/31 | (2006.01) |
| H01J 37/26 | (2006.01) |

(52) U.S. Cl.
CPC ......... *G01N 1/28* (2013.01); *H01J 2237/31749* (2013.01); *H01J 2237/20214* (2013.01); *H01J 2237/20207* (2013.01); *H01J 37/31* (2013.01); *H01J 37/26* (2013.01)

(58) Field of Classification Search
CPC ......... H01J 37/26; H01J 37/208; H01J 37/31; H01J 37/3056; H01J 2237/31749; H01J 2237/20207; H01J 2237/208
USPC ................................................. 250/306–311
See application file for complete search history.

(56) References Cited

U.S. PATENT DOCUMENTS

| | | | |
|---|---|---|---|
| 2002/0079463 A1* | 6/2002 | Shichi et al. ............... | 250/492.1 |
| 2004/0084629 A1* | 5/2004 | Preikszas et al. ......... | 250/396 R |
| 2006/0011868 A1* | 1/2006 | Kidron et al. ............ | 250/492.22 |
| 2008/0113455 A1* | 5/2008 | Jain et al. .......................... | 438/8 |
| 2010/0243889 A1* | 9/2010 | Faber et al. .................... | 250/307 |
| 2012/0067718 A1* | 3/2012 | Cox ........................... | 204/192.33 |
| 2012/0248455 A1* | 10/2012 | Van Gestel ...................... | 257/75 |
| 2012/0253497 A1 | 10/2012 | Prager et al. | |
| 2013/0001591 A1 | 1/2013 | Wu et al. | |
| 2013/0240836 A1* | 9/2013 | Lee et al. ........................ | 257/19 |

OTHER PUBLICATIONS

R. Hull. "Microstructural Evaluation of Optical Materials and Devices Using a Combination of Focused Ion Beam Sputtering and Transmission Electron Microscopy," Optical Materials, v6, 1996, pp. 1-11.

(Continued)

*Primary Examiner* — Jack Berman
*Assistant Examiner* — Kevin Chung
(74) *Attorney, Agent, or Firm* — Keivan Razavi; Catherine Ivers

(57) ABSTRACT

A method of preparing a transmission electron microscopy (TEM) sample from a semiconductor structure may include milling a region of the semiconductor structure with a focused ion beam and generating the transmission electron microscopy (TEM) sample. The focused ion beam providing the milling may include a rotation angle relative to the crystallographic axis of the semiconductor structure. A transmission electron microscopy image of a cross-sectional plane of the generated transmission electron microscopy (TEM) sample may be generated using a transmission electron microscope, whereby the transmission electron microscopy image of the cross-sectional plane includes an image projection-free region based on the rotation angle.

20 Claims, 5 Drawing Sheets

(56) References Cited

OTHER PUBLICATIONS

J. Demarest and Z. DeSouza. "Start Up and Evolution of a FEI DA 300 DBFIB for Automatic STEM Sample Preparation," Proc 33rd International Symposium for Testing and Failure Analysis, San Jose, CA, Nov. 2009, pp. 334-338.

I. Jozwik-Biala, et al. "HRTEM Study of Track Evolution in 120MeV U Irradiated Gd2Ti2O7," Nuclear Instruments and Methods in Physics Research B, v286, 2012, pp. 258-261.

Ruprecht, et al. "A review of ULSI failure analysis techniques for DRAMs. Part II: Defect isolation and visualization." Microlectronics Reliability 43 (2003) 17-41.

Langford, et al. "In situ lift-out: Steps to improve yield and a comparison with other FIB TEM sample preparation techniques", Science Direct (2008) I325-I330.

Zschech, et al. "Physical failure analysis in semiconductor industry—challenges of the copper interconnect process", Science Direct (2003) 457-464.

Munroe. "The application of focused ion beam microscopy in the material sciences", Materials Characterization 60 (2009) 2-13.

http://www.fischione.com/products/model_1040.asp May 30, 2013. "Model 1040 NanoMill TEM speciman preparation system".

\* cited by examiner

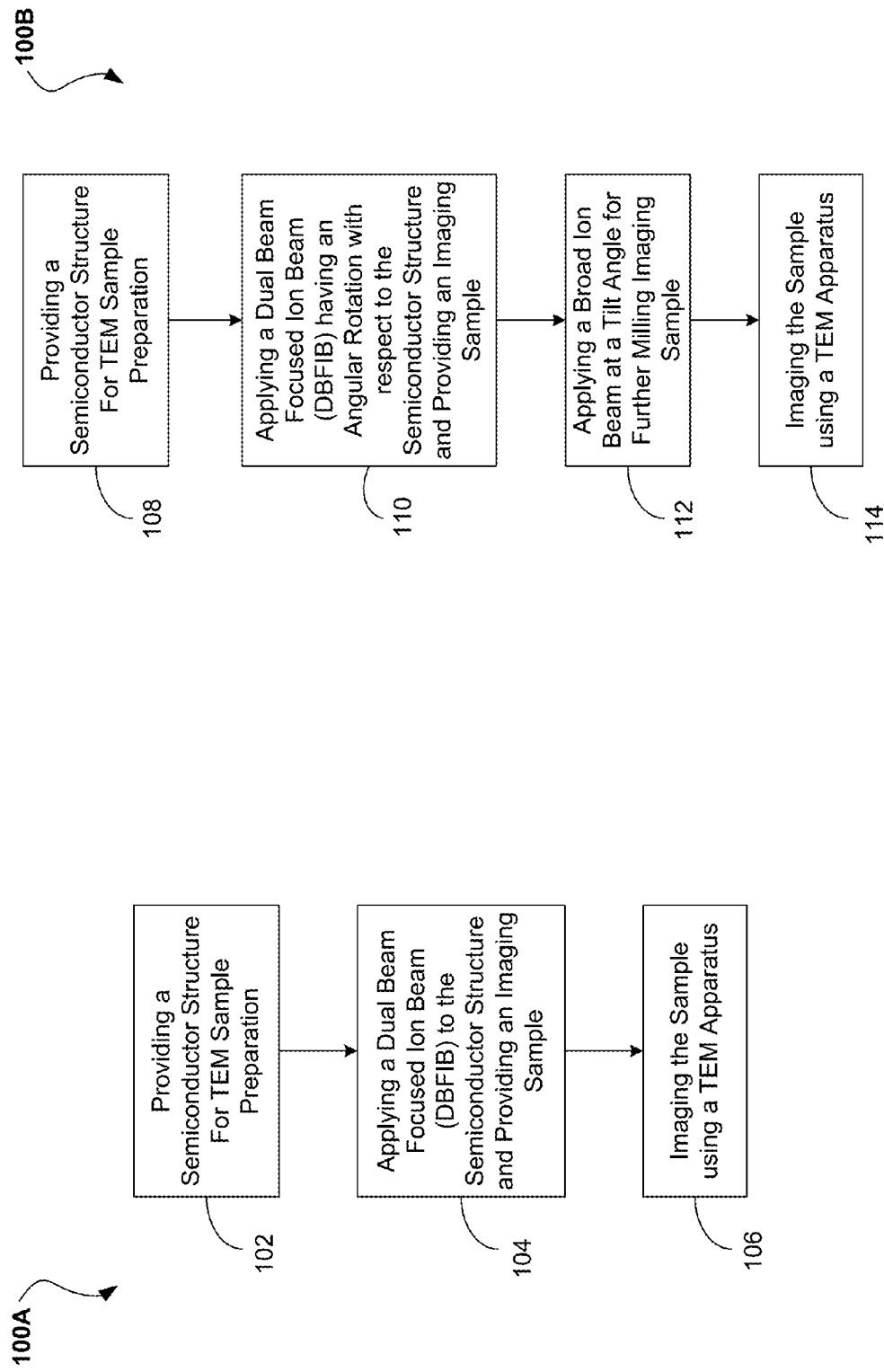

TRANSMISSION ELECTRON MICROSCOPE SAMPLE FABRICATION

BACKGROUND a. Field of the Invention

The present invention generally relates to semiconductor device imaging, and more particularly, to the preparation of semiconductor devices for such device imaging processes.

b. Background of Invention

Based on Moore's Law's the shrinking dimensions of, for example, semiconductor device structures (e.g., Field Effect Transistors), conventional transmission electron microscopy (TEM) techniques may be incapable of generating the thin sample thicknesses required for clearly imaging such structures. Accordingly, TEM sample preparation challenges may become more prevalent.

Automated TEM sample fabrication with instruments such as single and dual beam focused ion beams may include lamella thicknesses in the region of 100 nm. However, device and test structure dimensions may now contain multiple features within a 100 nm slice. This in turn may lead to projection effects which can obfuscate the features of interest and, thus, mask critical information associated with the fabricated sample.

It may, therefore, be desirable, among other things, to provide enhanced TEM sample preparation processes.

BRIEF SUMMARY

According to at least one exemplary embodiment, a method of preparing a transmission electron microscopy (TEM) sample from a semiconductor structure may include milling a region of the semiconductor structure with a focused ion beam and generating the transmission electron microscopy (TEM) sample. The focused ion beam includes a rotation angle relative to a crystallographic axis corresponding to the semiconductor structure. A transmission electron microscopy image of a cross-sectional plane of the generated transmission electron microscopy (TEM) sample is then generated using a transmission electron microscope, whereby the transmission electron microscopy image of the cross-sectional plane includes an image projection-free region based on the rotation angle.

According to at least one other exemplary embodiment, a method of preparing a transmission electron microscopy (TEM) sample from a semiconductor structure may include milling a region of the semiconductor structure with a focused ion beam, such that the focused ion beam includes a rotation angle relative to a crystallographic axis corresponding to the semiconductor structure. The milled region of the semiconductor structure is sputtered with a collimated ion beam for generating the transmission electron microscopy (TEM) sample. The collimated ion beam may include a tilt angle relative to a cross-sectional plane of the transmission electron microscopy (TEM) sample. A transmission electron microscopy image of the cross-sectional plane of the transmission electron microscopy (TEM) sample is then generated using a transmission electron microscope, whereby the transmission electron microscopy image of the cross-sectional plane includes an image projection-free region based on the rotation angle.

According to yet another exemplary embodiment, a method of preparing a transmission electron microscopy (TEM) sample from a semiconductor structure may include selecting a predetermined length corresponding to an image projection-free region. A region of the semiconductor structure is then milled with a focused ion beam for generating the transmission electron microscopy (TEM) sample, whereby the focused ion beam includes a rotation angle relative to a crystallographic axis corresponding to the semiconductor structure. The rotational angle is selected based on the predetermined length corresponding to the image projection-free region. A transmission electron microscopy image of a cross-sectional plane of the generated transmission electron microscopy (TEM) sample is generated using a transmission electron microscope, such that the transmission electron microscopy image of the cross-sectional plane includes the image projection-free region based on the rotation angle.

BRIEF DESCRIPTION OF THE SEVERAL VIEWS OF THE DRAWINGS

FIG. 1A is an operational flow diagram for preparing a TEM sample according to conventional methods;

FIG. 1B is an operational flow diagram for preparing a TEM sample according to an exemplary embodiment;

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

The following one or more exemplary embodiments describe a method of preparing a transmission electron microscopy (TEM) sample corresponding to a semiconductor device in a manner that enables a TEM image of the sample to include image projection-free regions. In particular, the one or more exemplary embodiments described below may be directed to mitigating or removing image projection effect while imaging, for example, device structural dimensions or 50 nm or less. Example device structures may include 3-dimensional semiconductor device structures such as FinFET devices.

Figure 2A:
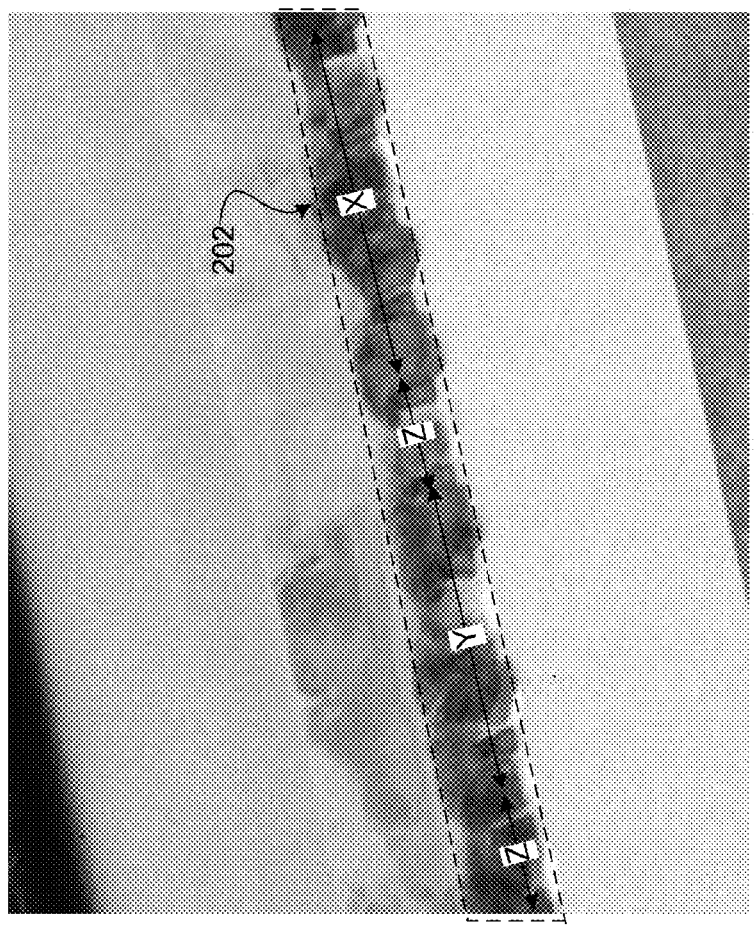
FIG. 2A is a TEM photographic image of an example TEM sample prepared using the conventional method of FIG. 1A.

FIG. 1A depicts an operational flow diagram 100A for preparing a TEM sample according to conventional methods. FIG. 1A will be described with aid of FIG. 2A and FIG. 3. At 102, a semiconductor structure such as semiconductor structure 300 (FIG. 3) is provided for preparing a TEM sample within a region of interest. For example, the region of interest may include a plurality of fin structures associated with a FinFET device within the semiconductor structure.

Figure 3:
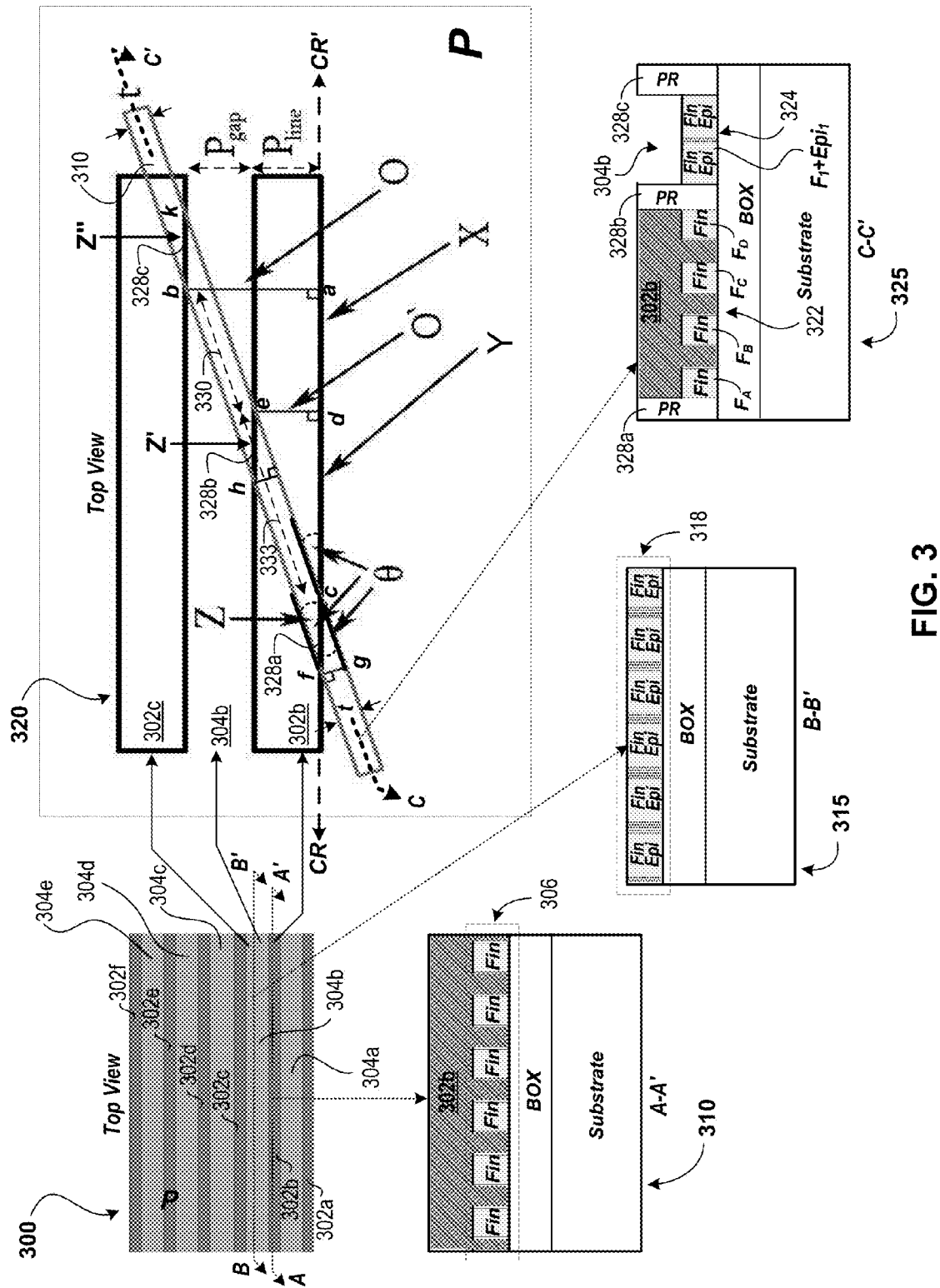
FIG. 3 is a schematic representation of a sample structure prepared according to the embodiment depicted in FIG. 1B.

Particularly, referring to FIG. 3, exemplary semiconductor structure 300 may include gate layers 302a-302f (i.e., PC lines). As further illustrated in the top view of semiconductor structure 300, gap regions 304a-304e, which are located between gate layers 302a-302f, may, for example, include epitaxially grown structures (e.g., Source/Drain regions). In some embodiments, back-end-of-the-line (BEOL) electrical interconnect structures (e.g., copper interconnects) and/or other semiconductor device features may be prepared and imaged according to the illustrated and described embodiments herein.

A cross section view 311 taken along axis A-A' of gate layer 302b may depict a plurality of fin structures 306, whereby the gate layer 302b is located both above and between the fin structures 306. Thus, a region of interest may include fin structures 306. The pitch of the fin structures 306 may be in the region of 40 nm. A cross section view 315 taken along axis B-B' of gap region 304b may illustrate a plurality of fin epitaxial structures 318.

Referring back to FIG. 1A, at 104, a milling tool such as a dual beam focused ion beam (DBFIB) may be used to create an imaging sample having a finite thickness that may have sample thicknesses ranging from about 10 nanometers (nm) to about 200 nanometers (nm). A combination of full wafer navigation, automation, site specific navigation, sputtering speed, and ion beam control in the creation of the sample image may efficiently facilitate electron transparency.

Referring to FIG. 3, for example, each of the gate layers 302a-302f (i.e., PC lines) may have a thickness of about 20 nm-40 nm, while each of the gap regions 304a-304e may include a thickness of 60 nm. By taking a sample of 100 nm thickness along an axis parallel to, or the same as, for example, axis A-A' of gate layer 302b or crystallographic axis CR-CR' of semiconductor structure 300, the prepared sample may include gate layers 302b and 302c, and gap region 304b.

Still referring to FIG. 1A, at step 106, a cross-section of the prepared sample, which includes gate layers 306b and 306c, and gap region 304b, may be imaged by a TEM apparatus. The imaging of the cross-section of the prepared sample, which is cut using the DBFIB along the crystallographic axis CR-CR' (i.e., no angular deviation), may yield an image that obfuscates certain feature of interests. For example, when the imaged feature of interest is the fin structures 306 (FIG. 3), other features within the sample such as the fin epitaxial structures 318 (FIG. 3), may be projected onto the image of the fin structures 306 (FIG. 3). This phenomenon is illustrated in TEM image 200A depicted in FIG. 2A. In the image 200A, the area within rectangle region 202 may depict the projection of the fin epitaxial structures 318 (FIG. 3) onto the fin structures 306 (FIG. 3) below gate layer 302b. Thus, the features of the fin structures 306 (FIG. 3) may not be clearly apparent in the TEM image 200A.

FIG. 1B depicts an operational flow diagram 100B for preparing a TEM sample according to an exemplary embodiment. FIG. 1B will be described with aid of FIG. 2B and FIG. 3. At 108, a semiconductor structure such as semiconductor structure 300 (FIG. 3) is provided for preparing a TEM sample within a region of interest. For example, the region of interest may include a plurality of fin structures associated with a FinFET device with the semiconductor structure.

As previously described, referring to FIG. 3, exemplary semiconductor structure 300 may include gate layers 302a-302f (i.e., PC lines). As further illustrated in the top view of semiconductor structure 300, gap regions 304a-304e, which are located between gate layers 302a-302f, may, for example, include epitaxially grown structures (e.g., Source/Drain regions).

The cross section view 311 taken along axis A-A' of gate layer 302b may depict the plurality of fin structures 306, whereby the gate layer 302b is located both above and between the fin structures 306. The pitch of the fin structures 306 may also be in the region of 40 nm. A cross section view 315 taken along axis B-B' of gap region 304b may illustrate the plurality of fin epitaxial structures 318.

Referring back to FIG. 1B, at 110, a milling tool such as a dual beam focused ion beam (DBFIB) may be used to create an imaging sample having a finite thickness that may have a sub 100 nm sample thickness. As previously described, referring to FIG. 3, each of the gate layers 302a-302f (i.e., PC lines) may have a thickness of about 20 nm-40 nm, while each of the gap regions 304a-304e may include a thickness of 60 nm.

In contrast to the process described in relation to FIG. 1A, according to operation flow 100B, a sample 310 (FIG. 3) of thickness t may be generated by milling semiconductor structure 300 along axis C-C', as depicted in the exploded top view 320 (FIG. 3) of gate layers 302b and 302c, and gap region 304b. Accordingly, semiconductor structure 300 (FIG. 3) may be milled at a predefined rotation angle θ (FIG. 3) relative to the crystallographic axis CR-CR' (FIG. 3) of semiconductor structure 300. Thus, in order to generate the sample 310 (FIG. 3) of thickness t, in some implementations, the semiconductor structure 300 and, therefore, the crystallographic axis CR-CR' (FIG. 3) of semiconductor structure 300, may be oriented at angle θ (FIG. 3) relative to the ion beam generated by the DBFIB tool. In other implementations, the ion beam generated by the DBFIB tool may be oriented at angle θ (FIG. 3) relative to the crystallographic axis CR-CR' (FIG. 3) of semiconductor structure 300.

As depicted in FIG. 3, the rotation angle θ may have a range of about 1 to 20 degrees. Typically, the rotation angle θ may be about 10 degrees. As illustrated in the exploded top view 320, the rotation angle θ may include an angular deviation within the top surface plane P of the semiconductor structure 300 taken from the crystallographic axis CR-CR'.

For example, a gallium DBFIB tool used to mill and prepare a sample such as sample 310 (FIG. 3) from semiconductor structure 300 may generate an ion beam column based on setting an accelerating voltage in the range of about 0.5 kV to about 50 kV (typically 5 kV and 30 kV), an ion beam current in the range of about 1 pA to about 10 nA (typically 50 pA-9 nA), and a tilt angle in the range of about 0 to about 52 degrees (typically +/−2 degrees during TEM sample fabrication). The material sputter rate may vary according the ion beam current and accelerating voltage, as well as tool design and set up. Moreover, the electron beam column of the DBFIB tool may include an accelerating voltage in the range of about 0.5-50 kV (typically 5 kV). The beam diameter of the ion beam may be about 1.0 nm to about 1000 nm, although small or larger beam diameters may be contemplated. Also, in operation, the ion beam may be rastered back and forth over a length having a range of about 3.0 μm to about 10.0 μm. However, the ion beam may typically be rastered over a length of about 3.0 μm.

Figure 4:
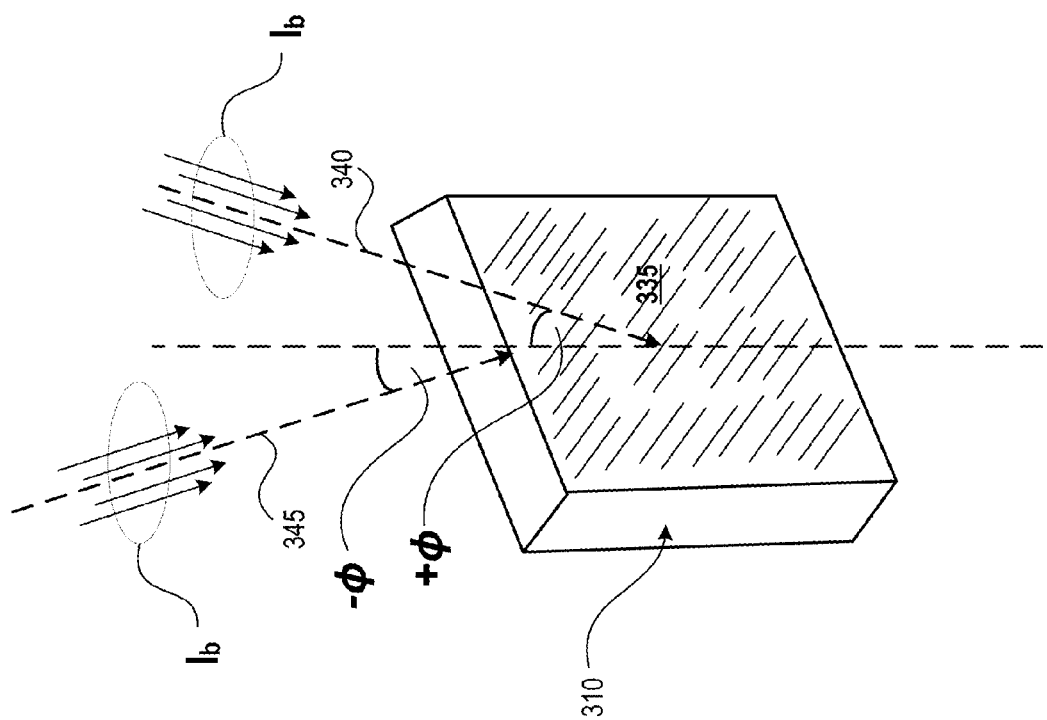
FIG. 4 is a 3-dimensional (3D) perspective view of the prepared sample structure according to one embodiment.

Referring to FIG. 1B, at 112, using an argon broad beam ion mill (e.g., Fischione® nanomill), sample 310 (FIG. 3) is further milled at a controlled and lower sputtering rate (e.g., 1 nm/min) to achieve desired thickness t. For example, referring to FIG. 4, the nanomill tool may be used to further mill sample 310, whereby the nanomill may generate a broad collimated ion beam $I_b$ by setting an accelerating voltage in the range of about 100 eV to 2000 eV (typically 900 eV), an emission current in the range of about 100 μA to about 200 μA (typically 130 μA), and a tilt angle ±φ in the range of 0 degrees to about ±20 degrees (typically ±10 degrees). The broad collimated ion beam $I_b$ may be rastered over a 15 μm by 15 μm rectangular region and include a spot size of about 1.0 μm to about 3.0 μm. It may be appreciated that a 0 eV accelerating voltage based on tool limits may also be contemplated. As depicted in FIG. 4, which shows a 3-dimensional view of sample 310, the tilt angle ±φ may be with reference to the cross section surface plane 335 of the sample 310. Axis 340 may be indicative of a positive tilt angle +ϕ relative to surface plane 335, while Axis 345 may be indicative of a negative tilt angle −ϕ relative to surface plane 335.

At 114, the cross-section view 325 (FIG. 3) of the prepared sample 310 (FIG. 3), which may include regions corresponding to gate layers 302b and 302c, and gap region 304b, may be imaged by a TEM apparatus. The imaging of the cross-section of the prepared sample 310 (FIG. 3), which is cut using the DBFIB at angle θ relative to the crystallographic axis CR-CR' (FIG. 3), may yield an image that mitigates or reduces the obfuscation of certain feature of interests. For example, when the imaged feature of interest is the fin structures 306 (FIG. 3), other features within the sample such as the fin epitaxial structures 318 (FIG. 3), may not cause image projection effects with respect to the fin structures 306 (FIG. 3).

Figure 2B:
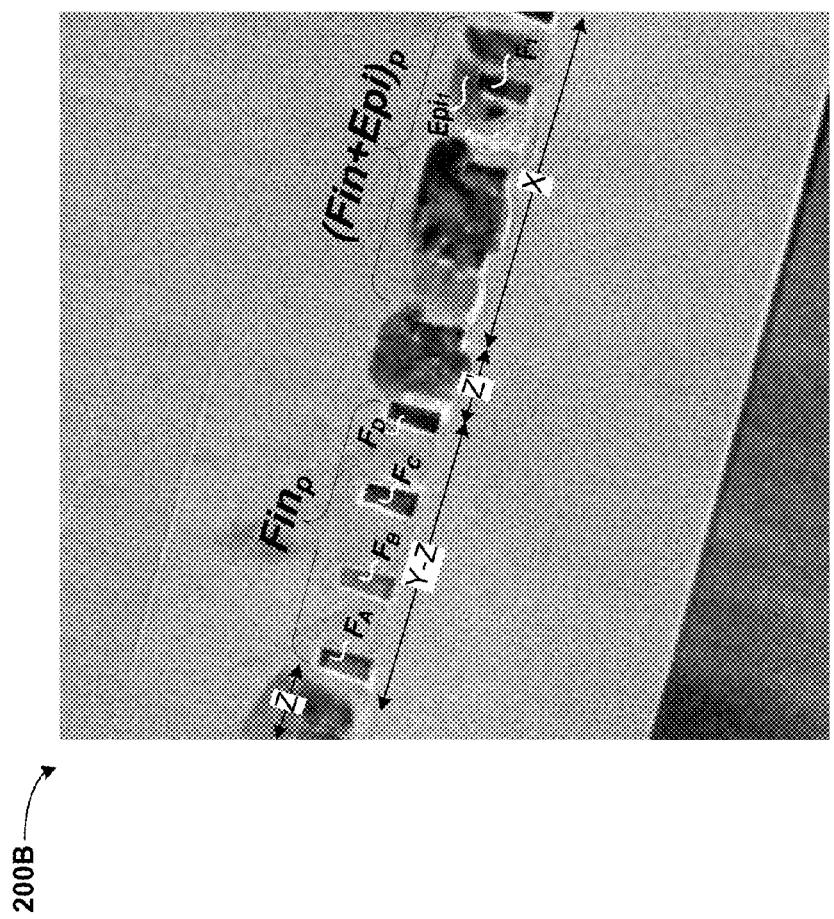
FIG. 2B is a TEM photographic image of an example TEM sample prepared using the exemplary embodiment of FIG. 1B.

This is illustrated in TEM image 200B depicted in FIG. 2B, which provides a TEM image of sample 310 (FIG. 3). In the image 200B, a portion $Fin_p$ of the fin structures 306 (FIG. 3) over region Y-Z of the sample 310 (FIG. 3) are imaged by the TEM with no projection effects. For example, over region Y-Z, fins $F_A$-$F_D$ (also see FIG. 3: cross section view 325) are clearly illustrated with no projection effects (i.e., a projection-free region). Moreover, as further depicted in TEM image 200B, region X of sample 310 (FIG. 3) also includes a projection-free region, whereby a portion $(Fin+Epi)_p$ of the fin structures and their corresponding epitaxial structures are shown (also see FIG. 3: cross section view 325). For example, over region X, fin $F_1$ and source/drain epitaxial structure $Epi_1$ corresponding to fin $F_1$ within region X is illustrated (also see FIG. 3: cross section view 325). Within TEM image 200B, regions Z are projection regions. The projection and projection-free regions associated within the TEM image of the prepared sample 310 (FIG. 3) are further described below with the aid of FIG. 3.

Referring back to FIG. 3, the prepared sample 310 may include regions corresponding to gate layers 302b and 302c, and gap region 304b. In the illustrated embodiment, the crystallographic axis CR-CR' of semiconductor structure 300 may run parallel to, or be the same as, axis A-A' of gate layer 302b. Cross sectional view 325 taken along axis C-C' of semiconductor structure 300 depicts the cross sectional view 325 of sample 310. As illustrated, the cross section view 325 of sample 310 includes a plurality of fin structures 322 located under gate layer 302b and a plurality of fin epitaxial structures 324 (i.e., fin+epi) located within the gap region 304b. Also shown in cross section view 325 is projection regions 328a-328c. The projection regions include regions whereby one of the features of the sample 310 obfuscates another feature of the sample during the TEM imaging process.

For example, referring to cross section view 325 and exploded view 320, projection region 328a (i.e., segment fc shown in view 325) may include image projection effects associated with a region of the fin epitaxial source/drain structures (not shown) located within the gap region 304a and a region of the fin structures 306 under gate layer 302b. Projection region 328a is located between point f and point c along the bottom edge of gate layer 302b, as depicted in exploded view 320.

Also, projection region 328b (i.e., segment he shown in view 325) may include image projection effects associated with another region of the fin epitaxial source/drain structures 318 located within the gap region 304b and another region of the fin structures 306 under gate layer 302b. Projection region 328b is located between point h and point e along the top edge of gate layer 302b, as depicted in exploded view 320.

Finally, projection region 328c (i.e., segment bk shown in view 325) may include image projection effects associated with yet another region of the fin epitaxial source/drain structures 318 located within the gap region 304b, and a region of the fin structures (not shown) under gate layer 302c. Projection region 328c is located between point b and point k along the bottom edge of gate layer 302c, as depicted in exploded view 320.

In contrast, still referring to cross section view 325 and exploded view 320, projection-free regions may exist, whereby designated features of the prepared sample 310 may be distinguished without undesirable image projections from other features of the sample 310. For example, portion 330 of the sample 310 located at region X between points a and d of the bottom edge of gate layer 302b may be projection-free and solely facilitate TEM imaging fin epitaxial structures 324 located within the gap region 304b. As indicated above, region X is illustrated in the TEM image 200B (FIG. 2) of sample 310. Moreover, for example, portion 333 of sample 310 located at region Y-Z (i.e., df−fc=dc) between points c and d of the bottom edge of gate layer 302b may be projection-free and solely facilitate TEM imaging fin structures $F_A$-$F_D$ located under gate layer 302b. Region Y-Z is also illustrated in the TEM image 200B (FIG. 2) of sample 310.

Referring still to FIG. 3, the exploded view 320 is utilized to derive a mathematical relationship between the rotation angle θ associated with generating the sample 310, the projection regions Z, Z', Z", the projection-free regions Y-Z, X, and the sample thickness t. Since the length of regions Z, Z', Z" are substantially the same, in the following derivations, region Z will be used to represent all regions Z, Z', Z". Based on right-hand triangle cfg, projection region Z (i.e., segment cf) may be defined as:

$$Z = \frac{t}{\sin\theta} \quad (1)$$

Whereby t is the sample 310 thickness and θ is the rotation angle.

The Y region may be determined based on right-hand triangle cde, such that:

$$\tan\theta = \frac{de}{cd} = \frac{P_{line}}{Y} \Rightarrow Y = \frac{P_{line}}{\tan\theta} \quad (2)$$

Whereby $P_{line}$ is the thickness of gate layer 302b and θ is the rotation angle.

The X region may be determined based on right-hand triangle abf, such that:

$$X = af - Z - Y \quad (3)$$

Whereby af may be determined from triangle abf, such that:

$$\tan\theta = \frac{ab}{af} = \frac{P_{line} + P_{gap}}{X + Y + Z} \quad (4)$$

$$X + Y + Z = \frac{(P_{line} + P_{gap})}{\tan\theta}$$

$$X = \left[\frac{(P_{line} + P_{gap})}{\tan\theta}\right] - Z - Y$$

Whereby $P_{line}$ is the thickness of gate layer 302b, $P_{gap}$ is the thickness of gap region 304b, and θ is the rotation angle.

Substituting equations (1) and (2) above for Z and Y, respectively, in equation (4), gives:

$$X = \left[\frac{(P_{line} + P_{gap})}{\text{Tan}\theta}\right] - \frac{t}{\text{Sin}\theta} - \frac{P_{line}}{\text{Tan}\theta} \quad (5)$$

Thus, using equations (2) and (5), projection-free regions Y and X may be determined based on the dimensions of $P_{line}$ (i.e., thickness of gate layer 302b) and $P_{gap}$ (i.e., thickness of gap region 304b), the rotation angle θ, and sample thickness t. Also, using equation (1), the projection regions 328a-328c may be determined based on the rotation angle θ, and sample thickness t.

For example, in order to generate a projection-free TEM image of fins $F_A$-$F_D$ located in region Y, a Y region of at least 80 nm length may be desired for imaging fins having a 40 nm pitch. If, for example, $P_{line}$ (i.e., thickness of gate layer 302b) is about 40 nm thick, then, based on equation (2), the rotation angle θ of the DBFIB tool relative to the crystallographic axis CR-CR' of the semiconductor structure 300 is set to about 14 degrees. In the given example (i.e., θ=14 degrees), the projection regions (i.e., Z) given by equation (1) are determined to be about 200 nm for a sample thickness of about t=50 nm. Further, in order to generate a projection-free TEM image of the fin epitaxial structures 324 located within region X, as indicated by portion 330 of the sample 310, equation (5) may be utilized. Thus, for a $P_{line}$ (i.e., thickness of gate layer 302b) of about 40 nm thick, a $P_{gap}$ (i.e., thickness of gap region 304b) of about 60 nm, a sample thickness of about t=50 nm, and a rotation angle θ of about 14 degrees, region X may be about 35 nm.

It may, therefore, be appreciated that the rotation angle and sample thickness values may be determined in order to generate practical values for both the X and Y regions, whereby the practical values may be directed to values that enable the imaging of a feature of interest (e.g., one or more fins of a 3-D semiconductor structure, BEOL copper interconnect lines, etc.) with sufficient resolution. For example, if the TEM image is desired to depict a few fins of 20 nm pitch, then region Y may in turn be required to be a minimum of at least 40 nm or more to see the multiple fins. Thus, θ and/or sample thickness t may be varied to accommodate such a result.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. A method of preparing a transmission electron microscopy (TEM) sample from a semiconductor structure, the method comprising:
   selecting a sample thickness for the transmission electron microscopy (TEM) sample;
   milling a region of the semiconductor structure with a focused ion beam and generating the transmission electron microscopy (TEM) sample, wherein during the milling that generates the transmission electron microscopy (TEM) sample having the selected sample thickness, the focused ion beam includes a rotation angle relative to a crystallographic axis corresponding to the semiconductor structure, wherein the rotation angle used to generate the TEM sample is determined based on the selected sample thickness and a length of an image projection region; and
   generating a transmission electron microscopy image of a cross-sectional plane of the generated transmission electron microscopy (TEM) sample using a transmission electron microscope,
   wherein the generated transmission electron microscopy image of the cross-sectional plane includes both an image of an image projection-free region and an image of the image projection region, the image of the image projection-free region having an imaged feature of interest associated with the TEM sample that is unobfuscated by an image of another feature associated with the TEM sample, and the image of the image projection region having an imaged feature of interest associated with the TEM sample that is obfuscated by the image of another feature associated with the TEM sample.

2. The method of claim 1, further comprising:
   sputtering the generated transmission electron microscopy (TEM) sample with a collimated ion beam, the collimated ion beam including a tilt angle relative to the cross-sectional plane of the transmission electron microscopy (TEM) sample.

3. The method of claim 1, wherein the focused ion beam is generated with a gallium dual beam focused ion beam milling system.

4. The method of claim 2, wherein the collimated ion beam is generated with an argon nano-milling system.

5. The method of claim 1, wherein the rotation angle comprises an angular range of about 1 degree to about 20 degrees, the rotation angle selected from the angular range based on a predetermined length corresponding to the image projection-free region.

6. The method of claim 1, wherein the focused ion beam comprises a spot size of about 1 nm to about 1000 nm.

7. The method of claim 6, wherein the focused ion beam is rastered back and forth over a length of about 3.0 μm to about 10.0 μm.

8. The method of claim 2, wherein the collimated ion beam comprises a spot size of about 1.0 μm to about 3.0 μm.

9. The method of claim 2, wherein the collimated ion beam comprises a sputter rate of about 1 nm per minute.

10. The method of claim 1, wherein the transmission electron microscopy (TEM) sample comprises a thickness of about 10 nm to about 200 nm.

11. The method of claim 1, wherein the generated transmission electron microscopy image comprises:
   an image of a first region of the semiconductor structure including at least one fin of a field effect transistor; and
   an image of a second region of the semiconductor structure including at least one epitaxial growth region of a field effect transistor,
   wherein the image of the second region is not projected onto the image of the first region and the image of the first region is not projected onto the image of the second region.

12. The method of claim 2, wherein the tilt angle comprises about 10 degrees relative to the cross-sectional plane of the transmission electron microscopy (TEM) sample.

13. The method of claim 8, wherein the collimated ion beam is rastered over a 15 μm by 15 μm rectangular region.

14. A method of preparing a transmission electron microscopy (TEM) sample from a semiconductor structure, the method comprising:

milling a region of the semiconductor structure with a focused ion beam, the focused ion beam including a rotation angle relative to a crystallographic axis corresponding to the semiconductor structure;

sputtering the milled region of the semiconductor structure with a collimated ion beam and generating the transmission electron microscopy (TEM) sample, the collimated ion beam including a tilt angle relative to a cross-sectional plane of the transmission electron microscopy (TEM) sample, wherein the rotation angle used to generate the TEM sample is determined based on a selected thickness corresponding to the TEM sample and a length of an image projection region; and generating a transmission electron microscopy image of the cross-sectional plane of the transmission electron microscopy (TEM) sample using a transmission electron microscope, wherein the generated transmission electron microscopy image of the cross-sectional plane includes both an image of an image projection-free region and an image of the image projection region, the image of the image projection-free region having an imaged feature of interest associated with the TEM sample that is unobfuscated by an image of another feature associated with the TEM sample, and the image of the image projection region having an imaged feature of interest associated with the TEM sample that is obfuscated by the image of another feature associated with the TEM sample.

15. The method of claim 14, wherein:
the focused ion beam is generated with a gallium dual beam focused ion beam milling system; and
the collimated ion beam is generated with an argon nanomilling system.

16. The method of claim 14, wherein:
the rotation angle comprises an angular range of about 1 degree to about 20 degrees; and
the tilt angle comprises about 10 degrees relative to the cross-sectional plane of the transmission electron microscopy (TEM) sample.

17. The method of claim 14, wherein:
the focused ion beam comprises a spot size of about 1 nm to about 1000 nm, the focused ion beam being rastered back and forth over a length of about 3.0 μm to about 10.0 μm; and
the collimated ion beam comprises a spot size of about 1.0 μm to about 3.0 μm.

18. The method of claim 14, wherein the transmission electron microscopy (TEM) sample comprises a thickness of about 10 nm to about 200 nm.

19. The method of claim 14, wherein the generated transmission electron microscopy image comprises:
an image of a first region of the semiconductor structure including at least one fin of a field effect transistor; and
an image of a second region of the semiconductor structure including at least one epitaxial growth region of a field effect transistor,
wherein the image of the second region is not projected onto the image of the first region and the image of the first region is not projected onto the image of the second region.

20. A method of preparing a transmission electron microscopy (TEM) sample from a semiconductor structure, the method comprising:
selecting a predetermined length corresponding to an image projection-free region associated with the TEM sample;
milling a region of the semiconductor structure with a focused ion beam and generating the transmission electron microscopy (TEM) sample, wherein during the milling that generates the transmission electron microscopy (TEM) sample, the focused ion beam includes a rotation angle relative to a crystallographic axis corresponding to the semiconductor structure, wherein the rotation angle used to generate the TEM sample is determined based on the selected predetermined length corresponding to an image projection-free region associated with the TEM sample and a selected thickness corresponding to the TEM sample; and
generating a transmission electron microscopy image of a cross-sectional plane of the generated transmission electron microscopy (TEM) sample using a transmission electron microscope, wherein the generated transmission electron microscopy image of the cross-sectional plane includes both an image of the image projection-free region and an image of an image projection region, the image of the image projection-free region having an imaged feature of interest associated with the TEM sample that is unobfuscated by an image of another feature associated with the TEM sample, and the image of the image projection region having an imaged feature of interest associated with the TEM sample that is obfuscated by the image of another feature associated with the TEM sample.

\* \* \* \* \*